(12) United States Patent
Rossi

(10) Patent No.: US 11,116,427 B2
(45) Date of Patent: Sep. 14, 2021

(54) BREATHING ACTIVITY MONITORING DEVICE, CORRESPONDING SYSTEM AND METHOD

(71) Applicant: STMicroelectronics S.r.l., Agrate Brianza (IT)

(72) Inventor: Stefano Rossi, Siena (IT)

(73) Assignee: STMICROELECTRONICS S.r.l., Agrate Brianza (IT)

( * ) Notice: Subject to any disclaimer, the term of this patent is extended or adjusted under 35 U.S.C. 154(b) by 295 days.

(21) Appl. No.: 16/259,254

(22) Filed: Jan. 28, 2019

(65) Prior Publication Data

US 2019/0231227 A1  Aug. 1, 2019

(30) Foreign Application Priority Data

Jan. 29, 2018  (IT) .................. 102018000002109

(51) Int. Cl.
*A61B 5/113* (2006.01)
*A61B 5/08* (2006.01)
*A61B 5/00* (2006.01)

(52) U.S. Cl.
CPC .......... *A61B 5/113* (2013.01); *A61B 5/0809* (2013.01); *A61B 5/0816* (2013.01); *A61B 5/6823* (2013.01); *A61B 5/721* (2013.01); *A61B 5/7225* (2013.01); *A61B 5/7257* (2013.01); *A61B 5/6831* (2013.01); *A61B 5/7239* (2013.01); *A61B 2505/09* (2013.01); *A61B 2562/0219* (2013.01); *A63B 2230/42* (2013.01)

(58) Field of Classification Search
CPC ............ A61B 5/08–0826; A61B 5/721; A61B 5/0205
See application file for complete search history.

(56) References Cited

U.S. PATENT DOCUMENTS 8,909,333 B2  12/2014  Rossi
9,510,768 B2  12/2016  Rossi
(Continued)

OTHER PUBLICATIONS

Johnstone et al., "Bioharness™ multivariable monitoring device. Part 1: Validity," *Journal of Sports Science and Medicine 11*, pp. 400-408, 2012.
(Continued)

*Primary Examiner* — Thaddeus B Cox
(74) *Attorney, Agent, or Firm* — Seed IP Law Group LLP

(57) ABSTRACT

A device for monitoring breathing activity of, e.g., athletes while exercising includes a breathing activity sensor configured to be worn by a wearer and to provide a breathing activity signal indicative of the breathing activity of the wearer. A motion sensor is configured to be worn by the wearer and to provide a motion signal indicative of the motion activity of the wearer. A processing arrangement is coupled to the breathing activity sensor to process the breathing activity signal and produce a processed breathing activity signal. The processing arrangement includes filter circuitry having a first filtering bandwidth and a second filtering bandwidth. The first filtering bandwidth is larger than the second filtering bandwidth. The filter circuitry is coupled to the motion sensor and operates with one of the first filtering bandwidth and the second filtering bandwidth selected as a function of the motion signal from the motion sensor.

20 Claims, 2 Drawing Sheets

(56) References Cited

U.S. PATENT DOCUMENTS

| | | | |
|---|---|---|---|
| 2005/0119586 A1* | 6/2005 | Coyle | A61B 5/4818 |
| | | | 600/538 |
| 2011/0112419 A1* | 5/2011 | Bjorling | A61B 5/363 |
| | | | 600/509 |
| 2011/0257553 A1 | 10/2011 | Banet et al. | |
| 2014/0343448 A1* | 11/2014 | Russell | A61B 5/721 |
| | | | 600/536 |
| 2015/0106052 A1* | 4/2015 | Balakrishnan | G06F 3/017 |
| | | | 702/150 |
| 2019/0021633 A1* | 1/2019 | Wang | A61B 5/0816 |

OTHER PUBLICATIONS

Kim et al., "Measurement Accuracy of Heart Rate and Respiratory Rate during Graded Exercise and Sustained Exercise in the Heat Using the Zephyr BioHarness™," *Int J Sports Med* 34(6), Jun. 2013, 10 pages.

Zheng et al., "Design and evaluation of a ubiquitous chest-worn cardiopulmonary monitoring system for healthcare application: a pilot study," *Med Biol Eng Comput* 55, pp. 283-294, 2017.

\* cited by examiner

BREATHING ACTIVITY MONITORING DEVICE, CORRESPONDING SYSTEM AND METHOD

BACKGROUND

Technical Field

The description relates to monitoring breathing activity (respiration) and one or more embodiments may be applied in the sports sector (both professional and amateur) as well as in fitness and wellness applications.

Description of the Related Art

Breathing monitoring plays a crucial role in the assessment and improvement of performance in "elite" athletes, since the respiration has the fundamental role of providing the oxygen needed by muscles to perform.

An accurate monitoring can be obtained through laboratory equipment, e.g., spirometry and capnography in conjunction with an exercise bike or a treadmill.

Using these devices may involve arranging what is essentially a clinical session, likely to provide at least some sort of discomfort and/or waste of time for the athlete and, possibly, his or her trainer, so that only a reduced number of such sessions may be planned over time. Solutions permitting "on-the-field" monitoring of the breathing activity of athletes (e.g., during high intensity exercise in daily training) with a view to improving performance may thus be desirable.

BRIEF SUMMARY

One or more embodiments may include a chest band, an electronic bio-impedance sensor and a motion sensor such as an acceleration sensor (both of these being of a type known in the art) along with a (hardware and/or software) processing module facilitating breathing rate monitoring with effective removal of undesired motion artifacts.

One or more embodiments may rely on the recognition that breathing and artifacts have different frequency bandwidths which can be separated through filtering.

One or more embodiments are based on the recognition that the signals involved may be (highly) non-stationary, with properties such as intensity and frequency that vary over time.

One or more embodiments may implement a tunable filtering procedure wherein the characteristics of a filtering action of breathing activity signals are "adjusted" as a function of accelerometer data.

In one or more embodiments the related processing may be embedded in a processing device such as a microcontroller.

One or more embodiments can operate adequately also during high-intensity exercise (e.g., running faster than 20 km/h), which facilitates daily monitoring including "on-the-field" monitoring with a level of accuracy comparable with state-of-the-art lab instruments intended for use in a lab environment and in connection with a treadmill or an exercising bike. One or more embodiments provide a wearable device which overcomes the limitations of currently available wearable devices, found to be accurate (only) with low-intensity activity, e.g., running up to 12-15 km/h, with a performance level quickly decreasing with intensity.

BRIEF DESCRIPTION OF THE SEVERAL VIEWS OF THE DRAWINGS

One or more embodiments will now be described, by way of example only, with reference to the annexed figures, wherein.

DETAILED DESCRIPTION

Figure 1:
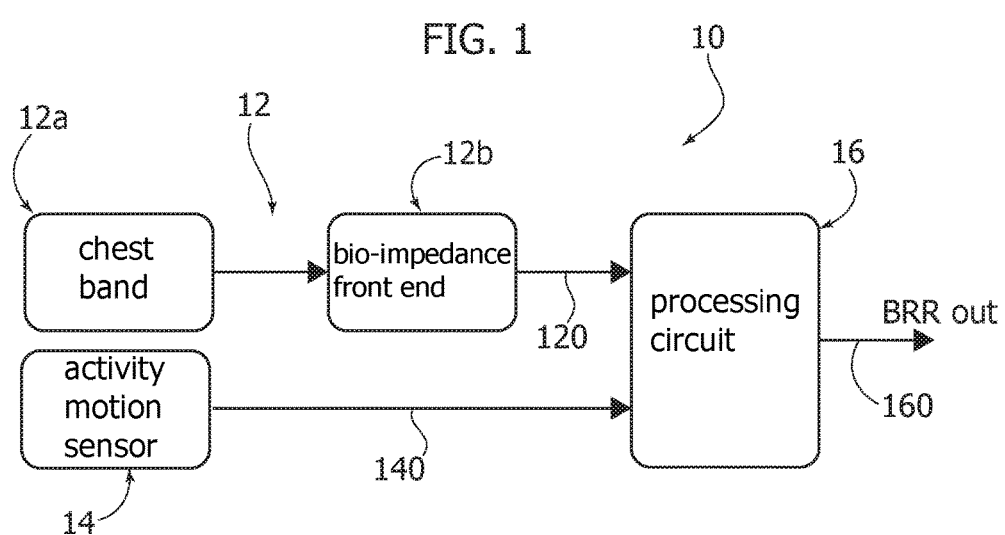
FIG. 1 is a functional block diagram of embodiments of the present disclosure.

In the ensuing description, one or more specific details are illustrated, aimed at providing an in-depth understanding of examples of embodiments of this description. The embodiments may be realized without one or more of the specific details, or with other methods, components, materials, etc. In other cases, known structures, materials, or operations are not illustrated or described in detail so that certain aspects of embodiments will not be obscured.

Reference to "an embodiment" or "one embodiment" in the framework of the present description is intended to indicate that a particular configuration, structure, or characteristic described in relation to the embodiment is included in at least one embodiment. Hence, phrases such as "in an embodiment" or "in one embodiment" that may be present in one or more points of the present description do not necessarily refer to one and the same embodiment. Moreover, particular conformations, structures, or characteristics may be combined in any adequate way in one or more embodiments.

The references used herein are provided merely for convenience and hence do not define the extent of protection or the scope of the embodiments.

Monitoring breathing activity (respiration) has been the subject of fairly intensive research.

For instance, some wearable devices for use in monitoring breathing activity are discussed in the literature and are also commercially available, as witnessed, e.g., by:

Zheng, J., et al.: "Design and evaluation of a ubiquitous chest-worn cardiopulmonary monitoring system for healthcare application: a pilot study", Medical and Biological Engineering and Computing, 55(2), 2017, pp. 283-291;

Johnstone, J. A., et al.: "Bioharness™ multivariable monitoring. Part I: Validity", Journal of Sports Science and Medicine, 11(3), 201, pp. 400-408;

Kim, J., et al.: "Measurement accuracy of heart rate and respiratory rate during graded exercise and sustained exercise in the heat using the Zephyr BioHarness™", International Journal of Sports Medicine, 34(6), pp. 497-501, 2013.

Detection of activity per se may be based, e.g., on inductive plethysmography, strain gauges, and so on.

As noted, conventional solutions are hardly capable of operating reliably at high running speeds (e.g., in excess of 12-15 km/h) of the wearer, with accuracy decreasing rapidly with increased activity intensity.

In that respect one may note that athletes can easily run at running speeds in excess of 20 km/h with a breathing rate up to, e.g., 60 breaths per minute (brpm).

As regards sensor technology, bio-impedance front-end circuits (as described, e.g., in U.S. Pat. Nos. 8,909,333 B2 and 9,510,768 B2, assigned to the instant Assignee) were found to be preferable to other types of sensors such as inductive plethysmography (measurement of inductance of a conductor around the chest, typically integrated in a band) or strain gauges in view of the possible intended use in a patch or in a chest band. Each of U.S. Pat. Nos. 8,909,333 B2 and 9,510,768 B2 is incorporated herein by reference in its entirety to the extent not inconsistent with the specific teachings and definitions provided herein.

These solutions were found to operate adequately in remote monitoring of cardiac and respiratory functions, also in connection with the activity level of a subject.

As noted, improved solutions are desirable in order to facilitate monitoring breathing activity (e.g., measuring breathing rate) in applications such as evaluating performance of athletes (e.g., in soccer/football teams). Ventilation is found to represent a significant parameter to monitor, e.g., in athletes while training insofar as adequate supply of oxygen to the muscles facilitates reaching good performance levels.

Ventilation can be estimated as a function of the breathing rate, possibly on the basis of calibration procedures (e.g., by establishing a relationship between breathing rate and ventilation in a certain athlete or in a certain group of sample athletes).

It is noted that the breathing activity signal may be negatively affected by artifacts related to motion of the wearer. It is similarly noted that breathing and associated artifacts generally lie in different frequency bands so that selective filtering may (notionally) permit artifact removal.

Conventional filtering may however turn out to be ineffective insofar as "large" filters (that is, filters with a large bandwidth) may be ineffective in filtering artifacts at low frequencies (e.g., running at low speed, reduced physical activity) which may result in an over-estimation of the breathing rate (BRR).

Conversely filters with narrow bandwidths may undesirably filter out "useful" signal, e.g., when the breathing rate increases due to increased activity, this possibly leading to an under-estimation of BRR.

In principle, these issues may be addressed by resorting to time-frequency approaches. This, however, may be computationally expensive, which makes such a solution hardly suitable for use in wearable devices.

The same also applies to adaptive filtering, a feedback approach based on the use of an artifact sensor capable of providing a signal with high correlation with the artifact component of the (bio-impedance) signal.

Again, while feasible in principle, such solutions are hardly practical in view of the complexity (and cost) of the associated circuitry. For instance, identifying an artifact sensor exhibiting high correlation with the artifact component of the signal is far from easy. Also, signals from simple and cheap motion sensors, e.g., accelerometers, are highly correlated with the movements, but the actual effect of the movements on the bio-impedance signal depends on many factors and the coupling factor is usually complex and not linear. The result is that the accelerometer signal exhibits a poor correlation with the artifact component of the bio-impedance signal, and this makes the use of adaptive filtering ineffective.

Specifically, less "cumbersome" arrangements are desirable which may permit real-time monitoring of the breathing rate (BRR) in athletes, including "elite" athletes, e.g., while exercising, without having to resort to a specific environment (treadmill, bike and so on).

Wearable devices for monitoring breathing activity have been made available recently, primarily for medical use. Notionally, these devices could be applied to monitoring breathing activity in athletes. However, they may be severely affected by motion artifacts and their performance quickly decreases with the intensity of exercise.

Effectively countering artifacts related to motion may pave the way to using these technologies in monitoring performance in a more continuous and reliable way, also facilitating monitoring of breathing activity also in amateur sport and personal fitness applications, improving the effectiveness of training programs and opening new exploitation opportunities.

One or more embodiments address these issues by resorting to adjustable filtering, e.g., filtering involving plural filtering characteristics (e.g., distinct filters or a single adjustable filter) whose corner frequency (cut-off frequency or break frequency, according to other current designations) can be changed as a function of certain detected properties of the artifacts. For instance, these may be obtained from an accelerometer signal, thus giving rise to a forward system adapted to be implemented easily, reliably and at a low cost.

In one or more embodiments as exemplified in FIG. 1, a device 10 for monitoring breathing activity (respiration) may include a breathing activity sensor 12 configured to be worn by a wearer to provide a breathing activity signal over a line 120.

In one or more embodiments, the sensor 12 may include a chest band 12a to be worn by the wearer with a set of electrodes (e.g., four electrodes as conventional in certain chest bands for use, e.g., in sensing heart rate) coupled, e.g., to a bio-impedance front end 12b including, e.g., an analog front end receiving bio-impedance signals from the sensors in the chest band 12a and an analog-to-digital converter (ADC) to convert into digital signals the signals received from the sensors.

In one or more embodiments, the breathing activity sensor exemplified as 12 herein may substantially correspond to the arrangements disclosed in U.S. Pat. No. 8,909,333 B2 and U.S. Pat. No. 9,510,768 B2 (already cited).

In one or more embodiments, the device 10 may also include an activity (motion) sensor 14 similarly adapted to be worn by the wearer of the breathing activity sensor 12 and to provide over a line 140 signals indicative of the activity of the wearer (e.g., motion). An accelerometer (of any conventional type) is exemplary of a sensor 14 as considered herein.

The signals provided over the line 120 (breathing activity) and the line 140 (motion activity) are fed to a processing circuit 16 (e.g., a microcontroller unit, per se of a conventional type) which may be configured—as discussed in the following—to produce on an output line 160 a processed breathing activity signal BRRout resulting from a processing action intended to counter undesirable artifacts affecting the breathing activity signal.

The whole of the device 10 can be configured as a wearable device, e.g., incorporated in a chest band.

Figure 2:
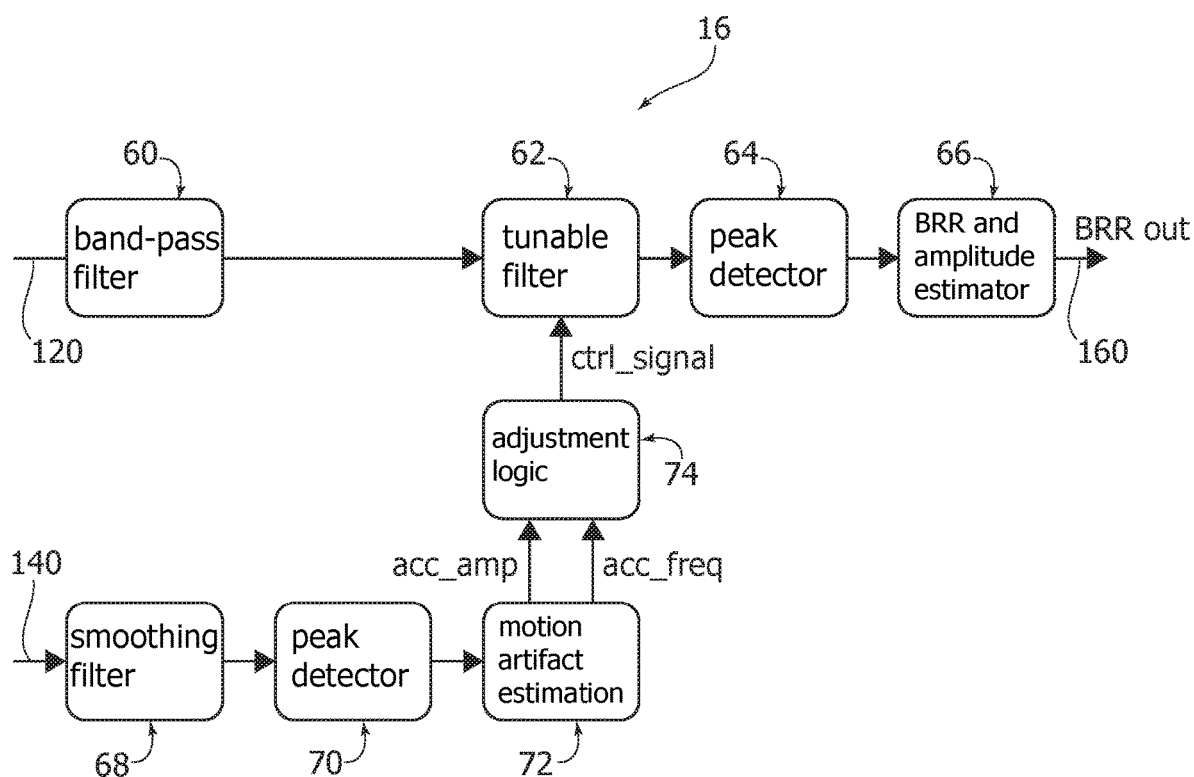
FIG. 2 is a further block diagram exemplary of certain possible features of embodiments of the present disclosure.

The block diagram of FIG. 2 is exemplary of a possible circuit arrangement of the processing circuit 16.

In one or more embodiments as exemplified herein, the breathing activity signal from the sensor 12 is supplied over the line 120 to a (fixed frequency) band-pass filter 60 followed by a tunable filter circuit 62.

As exemplified in FIG. 2, the filtered signal obtained from tunable filtering at 62 can be supplied to a peak detector circuit 64 followed by a breathing rate (BRR) and amplitude estimator circuit 66 to provide a processed breathing activity signal BRRout (e.g., signal indicative of the breathing rate-BRR) as an output.

The motion signal (accelerometer signal) received over the line 140 is fed to a smoothing filter 68 followed by a peak detector circuit 70 in turn followed by a (motion artifact) frequency and amplitude estimation circuit 72.

Signals acc_amp and ace_freq indicative of the amplitude (acc_amp) and frequency (acc_freq) of the motion signal received over the line 140 are applied to adjustment logic 74 configured to provide a control signal ctrl_signal to the tunable filter arrangement 62.

In general, embodiments of the present disclosure sense the intensity of the motion signal, where in the described embodiments the motion signal is an acceleration signal indicating the acceleration of the wearer. The motion signal is not limited to an acceleration signal, however, but instead may be a signal sensing other types of motion of the wearer. The intensity of the motion signal includes the amplitude of the motion signal, where the sensed amplitude may be the peak amplitude, peak-to-peak amplitude, or root mean square (RMS) amplitude of the motion signal. The intensity of the motion signal may also correspond to the energy or power of the motion signal.

In addition to intensity of the motion signal, embodiments of the present disclosure sense the frequency of the motion signal. Where the motion signal an acceleration signal, the frequency of this acceleration signal may be determined as described for the embodiments of FIGS. 1-5 of the present disclosure. The frequency of the motion signal may also be determined in other ways in further embodiments of the present disclosure. For example, a Fourier Transform or other frequency-domain analysis of the motion signal may be performed to extract frequency information about the motion signal, with this frequency information then being utilized in selecting the filtering of the breathing or respiratory signal.

Other than for the details expressly provided in the following, the various circuit blocks exemplified in FIG. 2 may per se be conventional in the art, thus making it unnecessary to provide a more detailed description herein. By way of example, in one or more embodiments, the filters 60, 68 may include standard filters intended to reduce the noise in the breathing activity signal and the motion signal received over the lines 120, 140 in order to reduce the noise outside the bandwidth of interest for evaluating the respective signals.

For instance, the filter 60 may be a band-pass filter with a bandwidth of, e.g., 0.1-1 Hz, and the filter 68 may be a low-pass filter with a bandwidth of, e.g., 7 Hz.

Still by way of example, the blocks 64 and 70 may implement (in a manner known per se) peak and valley detection procedures so that the blocks 66 and 72 cascaded thereto (that is, arranged downstream thereof) can calculate:

amplitude values, e.g., the average values of (all) the peak-to-valley amplitudes over a certain time window, with peak-to-valley amplitudes being the differences between a peak in the signal and the following valley, frequency values by counting the number of acts (peaks and/or valleys) occurring over a certain time window, which may otherwise be the same time window discussed above. As mentioned above in relation to the motion signal, techniques other than the peak-to-valley amplitude detection and frequency determination by counting peaks and/or valleys as described for the embodiment of FIG. 2 may also be utilized in processing the breathing activity signal.

Operation as described (e.g., operating over sliding time observation windows or periods) may facilitate "dynamic" operation of the system with the capability of taking into account variations over time of, e.g., the intensity of physical activity of the wearer.

Figure 3:
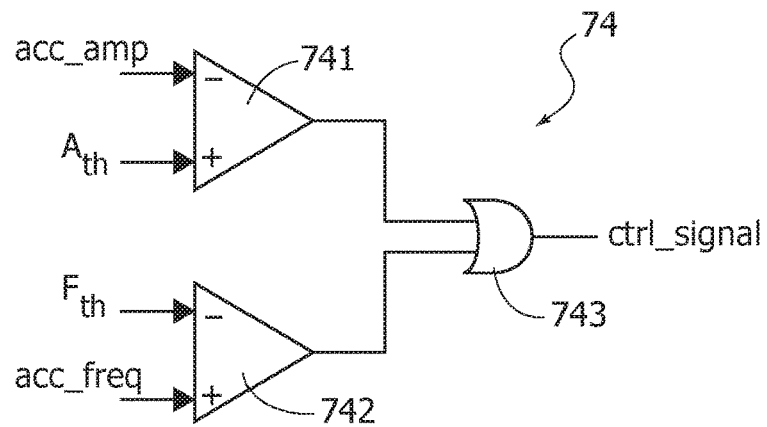
FIG. 3 is an exemplary circuit diagram of possible implementation details of embodiments of the present disclosure.

As exemplified in FIG. 3, the adjustment logic 74 may include two comparators 741, 742 wherein the signals acc_amp and acc_freq are compared with respective amplitude and frequency thresholds, $A_{th}$ and $F_{th}$, with the output from the comparators 741, 742 coupled, e.g., via an OR gate 743 which provides the control signal ctrl_signal to the tunable filter arrangement 62.

For instance, in one or more embodiments, the tunable filter arrangement 62 can be regarded as including a first filter and a second filter such as, e.g., Butterworth IIR filters ($6^{th}$ order) having corner frequencies (that is, cut-off or break frequencies) equal to about 1 Hz and 0.5 Hz.

As noted, in one or more embodiments, implementing the corresponding filter characteristics do not necessarily involve using two (or more) physically distinct filter structures (which are considered herein merely for the sake of simplicity of description). One or more embodiments may in fact include a software implementation of an adjustable (tunable) filter arrangement 62.

For instance, in one or more embodiments, a possible adjusting filtering logic may include using a first filter having a higher or larger bandwidth (e.g., a low-pass filter characteristic with a corner frequency at about 1 Hz) and a second filter having a lower or narrower bandwidth (e.g., a low-pass filter with a corner frequency at about 0.5 Hz).

For instance, in the arrangement here exemplified by means of the comparators 741 and 742 (which, as the whole of the processing exemplified herein can be performed via HW and/or SW means) the signal ctrl_signal output from the OR gate 743 (a high output if one or both the inputs are high) goes to, e.g., "1", thus causing the largest filter (namely the first filter having a larger bandwidth) to be used when one or both the outputs from the comparators 741 and 742 go to "1".

In one or more embodiments as exemplified in FIG. 3, $A_{th}$ and acc_freq are applied to the non-inverting inputs of the comparators 741, 742 with acc_amp and $F_{th}$ applied to the inverting inputs so that the outputs from the comparators 741 and 742 (input to the gate 743) going to a logic level "1" may correspond to the following conditions:

the signal acc_amp (artifact amplitude) is lower than the threshold value $A_{th}$ of the first comparator 741,
the signal acc_freq (artifact frequency) is higher the threshold value $F_{th}$ of the second comparator 742.

By resorting to such an (merely exemplary) logic:
if acc_amp is lower than the threshold $A_{th}$ or acc_freq is higher than the threshold $F_{th}$, the "larger" filter will be used,
else, the "narrower" filter will be used.

As exemplified herein, the signal from the tunable filtering arrangement 62 may be subjected to amplitude and frequency estimation (see the blocks 64 and 66) as discussed previously, thus providing a processed signal BRRout indicative of the intensity (amplitude) and the rate (frequency) of breathing activity.

Such signals are adapted to be exploited in various ways, e.g., in view of possible presentation/recordal for use by the wearer, a trainer/coach, a physician and so on.

Figure 4:
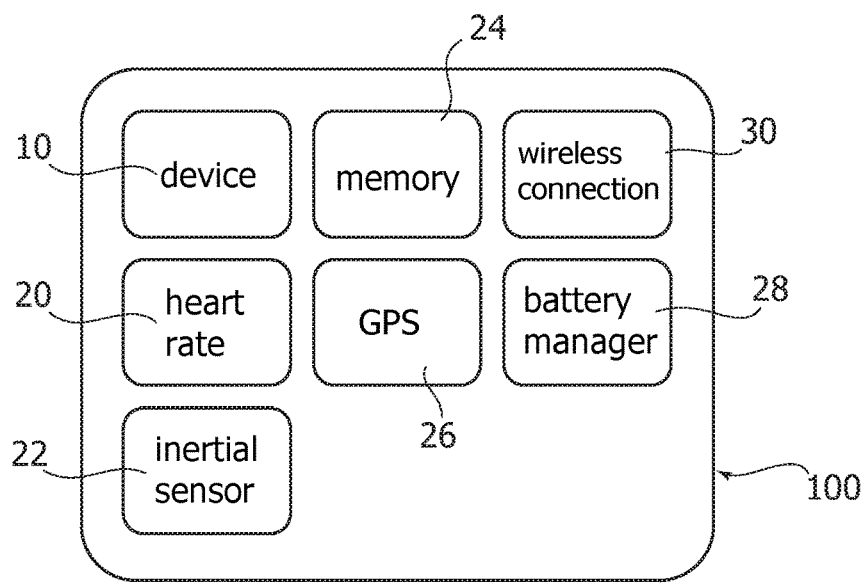
FIG. 4 is a block diagram of a system according to embodiments of the present disclosure.

For instance, FIG. 4 is exemplary of a system 100 where a device 10 as discussed previously may be associated with one or more other devices such as, e.g., a heart rate monitor 20, an inertial sensor 22, a memory 24 (adapted for storing signals as received from 10, 20 and/or 22), a GPS location sensor 26, a battery manager 28 (for a portable system).

Figure 5:
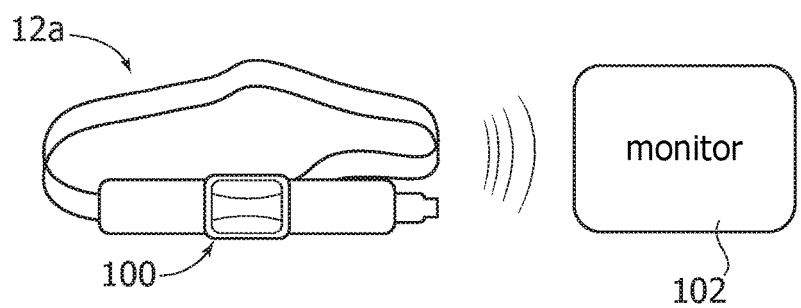
FIG. 5 exemplifies the wearable nature of embodiments of the present disclosure.

In such a system, signals from the device 10 (as possibly stored in the memory 24) and possibly other signals generated in the various other devices exemplified can be sent via a wireless connection 30 from the system 100 (which is suited to be carried by the chest band 12a as exemplified in FIG. 5) towards a monitor unit 102 such as a smart phone (for personal use) or other equipment for professional team-monitoring.

In one or more embodiments the smart phone or other equipment can be equipped (e.g., via an "app") with software facilitating further processing of the signals received from the system 100, including fairly sophisticated processing for training purposes.

The possible use of bio-impedance sensors has been considered herein (e.g., of the type discussed in U.S. Pat. No. 8,909,333 B2 or U.S. Pat. No. 9,510,768 B2) by way of example. Various other types of sensors, e.g., as discussed in the introductory portion of the description, may be used in one or more embodiments for producing the breathing activity (respiration) signal.

Also, while an exemplary type of procedure, based on detection of peaks and valleys has been described for calculating the amplitude/frequency of the motion artifacts (and the breathing activity signal), other procedures may be used for the same purpose as known in the art. For example, as discussed above, in general motion artifacts of the motion signal and the breathing activity signal may be processed in other manners than as described in relation to the embodiments of FIGS. 1-5 of the present disclosure. In general, embodiments of the present disclosure sense the intensity and frequency of the motion signal and breathing activity signal. The intensity may be the amplitude, such as the peak-to-peak amplitude, peak amplitude, or RMS amplitude of the signal, and may also correspond to the energy or power of the signal. Similarly, the frequency of the motion or breathing activity signal may also be determined in other ways in further embodiments of the present disclosure, such as through Fourier Transform or other frequency-domain analysis.

Additionally, the dynamic adjustment filtering approach exemplified herein in connection with two filtering characteristics (e.g., 1 Hz and 0.5 Hz cutoff), which is suitable to be implemented both as distinct filters and as a single tunable filter, can be extended to a higher number of filtering characteristics.

One or more embodiments were found to be suitable for use together with heart rate meters and other technologies used in a monitoring athlete performance.

One of more embodiments were found to provide improved performance in comparison with conventional adaptive filtering where filter coefficients are based on a procedure which reduces the error between reference signal and the sensing signal received.

Such a feedback approach was found to operate adequately (only) when the reference signal is highly correlated with one of the components of the signal received (e.g., the noise/artifact component) and only marginally correlated with the other component (e.g., the breathing activity signal). It is noted that these conditions are hardly met in reality insofar as, e.g., the transfer function from movement to impedance artifact may turn out to be complex and non-linear with a poor correlation with an acceleration.

One or more embodiments thus facilitate on-the-field monitoring of breathing activity of athletes with good accuracy even in the presence of severe motion artifacts as possibly generated during high-intensity physical exercise.

Experimentation (eight acquisitions on six athletes) performed by comparing BRR signals obtained through the system here disclosed with BRR signals obtained through a reference system (capnography), indicated a mean error equal to 0.22 and a standard deviation equal to 1.2 with activity corresponding to running at increasing speed, up to the athlete maximal limit, resulting in speeds exceeding 20 Km/h with BRRs up to 55 brpm.

A device (e.g., 10) according to one or more embodiments may include:
  a breathing activity sensor (e.g., 12) configured (e.g., 12a, 12b) to be worn by a wearer and to provide a breathing activity signal (e.g., 120) indicative of the breathing activity of the wearer,
  a motion sensor (e.g., 14) configured (e.g., 12a) to be worn by said wearer and to provide a motion signal (e.g., 140) indicative of the motion activity of the wearer,
  a processing arrangement (e.g., 16) coupled to the breathing activity sensor, the processing arrangement configured (e.g., 60, 62, 64, 66) to process the breathing activity signal and produce therefrom a processed breathing activity signal (e.g., BRRout), the processing arrangement (16) including filter circuitry (e.g., 62) having at least a first filtering bandwidth and a second filtering bandwidth, the first filtering bandwidth being larger than the second filtering bandwidth, the filter circuitry in the processing arrangement coupled (e.g., at 74) to the motion sensor and configured to operate with one of the first filtering bandwidth and the second filtering bandwidth selected as a function of the motion signal from the motion sensor.

Reference being made in the foregoing to "at least" a first filtering bandwidth and a second filtering bandwidth is intended to highlight the fact that—as noted previously—the dynamic adjustment filtering approach exemplified herein in connection with two filtering characteristics (e.g., 1 Hz and 0.5 Hz cutoff) can be extended to a higher number of filtering characteristics.

In one or more embodiments, the breathing activity sensor may include a bio-impedance sensor, e.g., as disclosed in U.S. Pat. No. 8,909,333 B2 and U.S. Pat. No. 9,510,768 B2.

In one or more embodiments, the first filtering bandwidth and the second filtering bandwidth may have corner frequencies at 1 Hz and 0.5 Hz, respectively.

In one or more embodiments, the processing arrangement may include motion sensing circuitry (e.g., 70, 72) sensitive to an acceleration signal (140) from the motion sensor, the motion sensing circuitry having an amplitude threshold (e.g., $A_{th}$, 741) and a frequency threshold (e.g., $F_{th}$, 742), the motion sensing circuitry coupled to the filter circuitry and configured to activate the filter circuitry with the first filtering bandwidth as a result (e.g., 743) of the acceleration signal from the motion sensor having one or both of:
  an amplitude below the amplitude threshold,
  a frequency above the frequency threshold.

In one or more embodiments, the motion sensing circuitry may include:

a detection block (e.g., 70) configured to detect occurrence of peaks and valleys in the acceleration signal from the motion sensor, and an estimation block (e.g., 72) coupled to the detection block and configured to calculate:

a) an amplitude (e.g., acc_amp) of the acceleration signal from the motion sensor as a function of differences between peaks and valleys in the acceleration signal from the motion sensor, b) a frequency (e.g., acc_freq) of the acceleration signal from the motion sensor as a count of said peaks and valleys.

In one or more embodiments, the processing arrangement may include, arranged downstream said filter circuitry (e.g., 62) breathing activity sensing circuitry including:

a respective detection block (e.g., 64) configured to detect occurrence of peaks and valleys in the breathing activity signal output from said filter circuitry, and a respective estimation block (e.g., 66) coupled to the respective detection block and configured to produce said processed breathing activity signal (BRRout) by calculating:

a) an amplitude of the processed breathing activity signal (e.g., BRRout) as a function of differences between peaks and valleys in the breathing activity signal output from said filter circuitry, b) a frequency of the processed breathing activity signal as a count of said peaks and valleys.

In one or more embodiments, said estimation block and/or said respective estimation block may be configured to calculate said differences between peaks and valleys and said count of peaks and valleys over sliding time windows.

A system (e.g., 100) according to one or more embodiments may include:

a device according to one or more embodiments, including said breathing activity sensor and said motion sensor, the device (10) wearable by a wearer, a transmitter device (e.g., 30) configured to transmit the processed breathing activity signal from the device to a monitoring circuit (e.g., 102).

In one or more embodiments, the transmitter device may include a wireless transmitter configured to transmit the processed breathing activity signal to a remote monitoring circuit.

A method according to one or more embodiments may include:

sensing a breathing activity signal indicative of the breathing activity of a wearer via a breathing activity sensor worn by the wearer, sensing a motion signal indicative of the motion activity of said wearer via a motion sensor worn by said wearer, processing the breathing activity signal via a processing arrangement worn by said wearer and producing therefrom a processed breathing activity signal, wherein processing includes filtering the breathing activity signal by applying selectively one of at least a first filtering bandwidth and a second filtering bandwidth, the first filtering bandwidth being larger than the second filtering bandwidth, wherein the filtering bandwidth applied is selected as a function of said motion signal.

The terms module, device, block, and unit as used herein correspond to suitable circuitry to implement the associated functionality of the module, device, block, or unit, where the "suitable circuitry" may include hardware, software, firmware, or any combination thereof. These terms and any similar terms utilized herein are not used as generic placeholders or nonce words for the term "means." Instead, the terms module, device, block, and unit are used in combination with associated structural modifiers to cover the corresponding circuitry described herein as well as any circuitry known to those skilled in the art or later developed, and equivalents of such circuitry.

Without prejudice to the underlying principles, the details and embodiments may vary, even significantly, with respect to what has been described by way of example only without departing from the extent of protection.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety to extent not inconstant with the teachings and definitions herein. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device, comprising:

a breathing activity sensor configured to be worn by a wearer and to provide a breathing activity signal indicative of a breathing activity of the wearer;

a motion sensor configured to be worn by said wearer and to provide a motion signal indicative of a motion activity of the wearer, the motion signal having an intensity and a frequency;

a processing circuit coupled to the breathing activity sensor and the motion sensor, the processing circuit configured to process the breathing activity signal and to produce therefrom a processed breathing activity signal, the processing circuit including filter circuitry having at least a first filtering bandwidth and a second filtering bandwidth, the first filtering bandwidth being larger than the second filtering bandwidth, and the filter circuitry configured to operate with the first filtering bandwidth to filter the motion signal responsive to the motion signal having at least one of the intensity below an amplitude threshold or the frequency above a frequency threshold, and the filter circuitry configured to operate with the second filtering bandwidth to filter the motion signal responsive to the motion signal having the intensity above or equal to the amplitude threshold or the frequency below or equal to the frequency threshold.

2. The device of claim 1, wherein the breathing activity sensor comprises a bio-impedance sensor.

3. The device of claim 1, wherein the first filtering bandwidth and the second filtering bandwidth have corner frequencies at 1 Hz and 0.5 Hz, respectively.

4. The device of claim 1, wherein the motion sensor comprises an accelerometer configured to generate an acceleration signal and the processing circuit further comprises motion sensing circuitry sensitive to the acceleration signal, the motion sensing circuitry having an amplitude threshold and a frequency threshold, and the motion sensing circuitry coupled to the filter circuitry and configured to activate the filter circuitry with the first filtering bandwidth based on the acceleration signal from the motion sensor having one or both of an amplitude below the amplitude threshold or a frequency above the frequency threshold.

5. The device of claim 4, wherein the motion sensing circuitry comprises:
a detection circuit configured to detect peaks and valleys in the acceleration signal; and
an estimation circuit coupled to the detection circuit and configured to calculate at least one of:
an amplitude of the acceleration signal as a function of differences between peaks and valleys in the acceleration signal; or
a frequency of the acceleration signal based on a count of said peaks and valleys.

6. The device of claim 5, wherein at least one of said estimation circuit or the estimation circuit is configured to calculate said differences between peaks and valleys and said count of peaks and valleys over sliding time windows.

7. The device of claim 4, wherein the processing circuit comprises breathing activity sensing circuitry coupled to the filter circuitry, the breathing activity sensing circuitry comprising:
a detection circuit configured to detect peaks and valleys in the breathing activity signal; and
an estimation circuit coupled to the detection circuit and configured to generate said processed breathing activity signal by calculating at least one of:
an amplitude of the processed breathing activity signal as a function of differences between the peaks and valleys in the breathing activity signal; or
a frequency of the processed breathing activity signal based on a count of said peaks and valleys.

8. A system, comprising:
a device configured to be wearable by a wearer, the device including:
a breathing activity sensor configured to generate a breathing activity signal indicative of a breathing activity of the wearer;
a motion sensor configured to generate a motion signal indicative of motion activity of the wearer, the motion signal including an intensity and a frequency; and
processing circuitry coupled to the breathing activity sensor and motion sensor, the processing circuitry configured to process the breathing activity signal to generate a processed breathing activity signal and configured to filter the motion signal with a first filtering bandwidth and a second filtering bandwidth, the first filtering bandwidth being larger than the second filtering bandwidth and the processing circuitry configured to select the first filtering bandwidth responsive to the motion signal having at least one of the intensity less than an amplitude threshold or the frequency greater than a frequency threshold, and the processing circuitry configured to select the second filtering bandwidth responsive to the motion signal not having at least one of the intensity less than the amplitude threshold or the frequency greater than the frequency threshold ; and
a transmitter device configured to transmit the processed breathing activity signal.

9. The system of claim 8, wherein the transmitter device further comprises a remote monitoring circuit and a wireless transmitter configured to transmit the processed breathing activity signal to the remote monitoring circuit.

10. The system of claim 8, wherein the breathing activity sensor comprises a bio-impedance sensor.

11. The system of claim 8, wherein the processing circuitry comprises filtering circuitry configured to be activated having the first filtering bandwidth with a corner frequency of 1 Hz and the second filtering bandwidth having a corner frequency of 0.5 Hz.

12. The system of claim 8, wherein the motion sensor comprises an accelerometer configured to generate an acceleration signal.

13. The system of claim 12, wherein the processing circuitry further comprises motion sensing circuitry coupled to receive the acceleration signal, the motion sensing circuitry configured to activate the filtering circuitry with the first filtering bandwidth based on the acceleration signal from the motion sensor having at least one of an amplitude below the amplitude threshold or a frequency above the frequency threshold.

14. The system of claim 13, wherein the motion sensing circuitry comprises:
a detection circuit configured to detect peaks and valleys in the acceleration signal; and
an estimation circuit coupled to the detection circuit and configured to determine an amplitude of the acceleration signal based on differences between peaks and valleys in the acceleration signal and configured to determine a frequency of the acceleration signal based on a count of the peaks and valleys.

15. The system of claim 14, wherein the processing circuitry comprises breathing activity sensing circuitry coupled to the filtering circuitry, the breathing activity sensing circuitry configured to detect peaks and valleys in the breathing activity signal and configured to generate the processed breathing activity signal based on an amplitude of the processed breathing activity signal as a function of differences between the peaks and valleys in the breathing activity signal and a frequency of the processed breathing activity signal based on a count of said peaks and valleys.

16. A method, comprising:
sensing a respiration of a wearer;
generating a respiration signal indicating the sensed respiration of the wearer;
sensing motion of the wearer, the sensed motion including a sensed intensity and a sensed frequency of the sensed motion;
filtering the respiration signal with a first filtering bandwidth and a second filtering bandwidth, the first filtering bandwidth being greater than the second filtering bandwidth;
selecting the first filtering bandwidth in response to the sensed intensity exceeding an intensity threshold and the sensed frequency exceeding a frequency threshold; and
selecting the second filtering bandwidth in response to the sensed intensity exceeding the intensity threshold and the sensed frequency being less than the frequency threshold.

17. The method of claim 16, wherein sensing motion of the wearer comprises sensing an acceleration of the wearer.

18. The method of claim 17, wherein the sensed intensity comprises one of an amplitude of the sensed acceleration, a root mean square value of the sensed acceleration, and an energy of the sensed acceleration.

19. The method of claim 18, wherein sensing the acceleration comprises:
sensing the amplitude of the acceleration; and
detecting peaks and valleys in the sensed amplitude of the acceleration; and sensing the frequency of the acceleration based on the detected peaks and valleys.

20. The method of claim 16, wherein sensing the respiration of the wearer comprises sensing a bio-impedance of the wearer.

\* \* \* \* \*